United States Patent [19]

Holloway

[11] Patent Number: 5,637,294

[45] Date of Patent: *Jun. 10, 1997

[54] GROOMING COMPOSITION

[76] Inventor: Trudy L. Holloway, 823 Fairdale Dr., Lexington, Ky. 40503

[*] Notice: The term of this patent shall not extend beyond the expiration date of Pat. No. 5,372,806.

[21] Appl. No.: 297,490

[22] Filed: Aug. 29, 1994

Related U.S. Application Data

[63] Continuation of Ser. No. 911,124, Jul. 9, 1992, Pat. No. 5,372,806, which is a continuation-in-part of Ser. No. 816,239, Jan. 3, 1992, abandoned.

[51] Int. Cl.$^6$ ............................................. A61K 7/075
[52] U.S. Cl. ................... 424/70.1; 424/70.12; 514/63; 514/762
[58] Field of Search .................. 424/70.11, 70.12, 424/70.1, 401, DIG. 1, 400, 70.121, 70.122, 70.31; 514/762, 63

[56] References Cited

U.S. PATENT DOCUMENTS

| | | | |
|---|---|---|---|
| 3,882,824 | 5/1975 | Acquaviva | 119/156 |
| 4,551,332 | 11/1985 | Stillman | 514/784 |
| 4,808,569 | 2/1989 | Chaudhuri et al. | 512/2 |
| 4,950,468 | 8/1990 | Nakamura et al. | 424/70.1 |

*Primary Examiner*—Neil S. Levy
*Attorney, Agent, or Firm*—Wood, Herron & Evans, L.L.P.

[57] ABSTRACT

A grooming composition includes by volume: 79.0%–91.0% water, 5.0–12.0% degreasifying agent (preferably, isoparaffinic hydrocarbon solvent), 0.5–3.5% conditioning and detangling agent (preferably, a silicone aqueous emulsion), 0.0–0.6% liquid vitamin E and 0.0–5.0% fragrance (preferably, vanilla flavoring).

4 Claims, No Drawings

GROOMING COMPOSITION

This application is a continuation of application Ser. No. 07/911,124, filed Jul. 9, 1992. U.S. Pat. No. 5,372,806, which is a continuation-in-part of U.S. patent application Ser. No. 07/816,239, filed Jan. 3, 1992, now abandoned.

TECHNICAL FIELD

The present invention relates generally to the grooming of the hair coat and, more particularly, to a unique composition particularly adapted for simplifying the grooming process and adding body and vigor to the hair receiving treatment.

BACKGROUND OF THE INVENTION

The care and grooming of domestic animals including domestic farm animals as well as show and race horses has long been an important concern in the field of animal husbandry. When preparing an animal for a sale, fair, show or other exposition, it is the desire of the groomer to ensure that the hair coat of the animal is clean, soft and shiny. The hair coat should also be manageable and full of body so that, for example, any cowlicks that are present may be trained to lay and stay where desired. Of course, any and all tangles and mats should be combed out of, for example, the tail and mane to enhance the appearance and beauty of the animal. For example, when grooming a horse for a show, it is not unusual for a groomer to spend several hours completing the task.

A need, therefore, is identified for a composition particularly adapted to ease the task of grooming the animal while also adding body, shine and manageability to the hair coat.

SUMMARY OF THE INVENTION

Accordingly, it is a primary object of the present invention to provide a grooming composition that is relatively easy and inexpensive to produce and that provides long term protection to the coat and skin of the animal being treated with the composition.

Another object of the present invention is to provide an improved grooming composition that simplifies the grooming process by allowing tangles and mats to be combed out more easily.

Yet another object of the present invention is to provide a grooming composition especially adapted to maintain the hair coat soft, shiny and manageable over an extended period of time, even following a bath.

Still another object of the invention is to provide an improved grooming composition that allows dirt, straw and other matter to be removed easily while also adding body and vigor to the hair coat so as to improve the overall healthful appearance of the animal. Accordingly, both cleaning and detailed grooming are provided in a one step process.

Other objects and advantages of the present invention will become apparent as the description thereof proceeds. In satisfaction of the foregoing objects and advantages, there is provided by this invention an improved grooming composition. The composition includes by volume substantially 79.0–91.0% water, 5.0–12.0% degreasifying agent miscible in water, 0.5–3.5% conditioning and detangling agent miscible in water, 0.0–0.6% liquid vitamin E and 0.0–5.0% fragrance agent.

The water functions as a carrier for the active agents of the composition. Preferably, the conditioning and detangling agent is a silicone aqueous emulsion. More particularly, a non-volatile, dimethyl polysiloxane emulsion (35% silicone) is utilized. The emulsion is of one oil-in-water type with a viscosity between 350 and 350,000 Cs. Such an emulsion is available, for example, from Union Carbide Chemical and Plastic Company of Danbury, Conn. under the trademark LE-45. It should be appreciated, however, that other volatile, non-volatile, linear or cyclic type oil-in-water silicone aqueous emulsions may be utilized. Advantageously, this agent conditions the hair adding body, vigor and shine. Further, the silicone aqueous emulsion allows tangles and mats to be removed more easily from the coat during brushing or combing. Accordingly, the grooming process is made easier on both the groomer and the animal and may be completed in a shorter time. Of course, it should be appreciated that other conditioning and detangling agents known in the art may also be utilized in the present composition.

The composition also includes a degreasifying agent that preferably is a hydrocarbon solvent such as an isoparaffinic hydrocarbon solvent having a hydrocarbon chain length between 6 and 14 and more preferably 7 and 8 carbon atoms. Such a solvent is available from Chemcentral, Inc. of Hamilton, Ohio, and sold under the trademark ISOPAR C. Advantageously, the isoparaffinic hydrocarbon solvent ensures that the grooming composition leaves no slick, greasy residue after use. Further, the solvent prevents undue buildup of the grooming composition in the hair coat that could otherwise eventually have a degrading effect on the shine and healthy appearance of the coat.

Vitamin E is provided in the composition to further soften and condition the hair coat and the skin. Additionally, a fragrance agent may be added to improve the scent of the composition and hence its appeal to the groomer and the animal receiving the treatment. Preferably, vanilla flavoring is utilized. It should be appreciated, however, that other fragrances and flavorings could be incorporated into the composition including for example, lemon oil, spearmint oil and wintergreen oil. Vanilla flavoring is preferred, however, as it also cuts grease and, therefore, enhances the cleaning effect of the composition upon initial application to the coat.

A preferred formulation for the grooming composition of the present invention comprises by volume substantially 84% water, 10% degreasifying agent miscible in water, 2.5% conditioning and detangling agent miscible in water, 0.5% liquid vitamin E and 3.0% fragrance agent.

DETAILED DESCRIPTION OF THE INVENTION

As indicated above, the present invention is drawn to novel compositions to be used in grooming. These compositions are particularly useful in a one step cleaning and grooming regimen that saves a significant amount of time when preparing an animal for a sale, fair, show or other exhibition. The compositions are also advantageously effective in removing tangles and mats from the coat. Further, the composition adds body and vigor to the coat which remains softer, shinier and more manageable for a significant time after use. This is true even after one or more intervening washings.

This is a significant advantage where the opportunity presents itself to dry sponge or brush dust from the coat between sale/show ring appearances. In this way the shiny appearance of the coat is fully restored to its original luster. In contrast, dry sponging or brushing fails to remove dust and dirt from the relatively tacky prior art grooming compositions. Accordingly, the animal groomed with a prior art composition is shown at a serious disadvantage to an animal groomed with the present composition. Further, it should be appreciated that these advantages of the present composition are achieved without leaving any slick or greasy residue that could tend to catch and hold dirt. Additionally, the product does not tend to build up over time.

The grooming composition comprises by volume, 79.0–91.0% water, 5.0–12.0% degreasifying agent miscible in water, 0.5–3.5% conditioning and detangling agent miscible in water, 0.0–0.6% vitamin E as a liquid and 0.0–5.0% fragrance agent.

The composition is prepared by adding the degreasifying agent, the conditioning and detangling agent as well as any vitamin E and fragrance agent to water contained in a mixing vessel of appropriate size. After stirring or other means of agitation to provide complete mixing of the ingredients, the composition may be added to a spray bottle for subsequent use.

Prior to use by the groomer, the spray bottle is shaken to provide complete mixing of the compositional ingredients. The composition is then sprayed onto a rub rag or cloth and then applied to the animal to be groomed by rubbing backwards through the hair. Alternatively, the composition may be directly sprayed onto the animal and then rubbed into the coat. Further, a grooming brush may be sprayed lightly as the composition aids in the removal of dirt and dandruff so as to leave the coat soft, shiny and clean. Thus, it should be appreciated that one step cleaning and grooming is possible. This significantly reduces grooming time. Accordingly, the groom has additional time to tend to other matters including the care and preparation of other animals or equipment.

The most preferred embodiment of the invention includes by volume 84% water, 10% degreasifying agent miscible in water, 2.5% conditioning and detangling agent miscible in water, 0.5% liquid vitamin E and 3.0% fragrance agent. Preferably, the degreasifying agent is a hydrocarbon solvent and, more particularly, an isoparaffinic hydrocarbon solvent having a hydrocarbon chain length between 6 and 14 and more preferably 7 and 8 carbon atoms. It should be appreciated, however, that other degreasifying agents known in the art may be utilized.

The conditioning and detangling agent is preferably a silicone aqueous emulsion. Such an emulsion should be of the non-volatile, oil-in-water with a viscosity of between 350 and 350,000 Cs. Preferably a linear or cyclic variety of silicone aqueous emulsion may be used such as a dimethylpolysiloxane. Once again, however, it should be appreciated that other known conditioning and detangling agents may be utilized. These include, for example, N-alkoxlated ether Z-pyrolidones, quaternary ammonium salt, quaternary imidazolinium salt, fatty alcohol, sorbitan ester, fatty acid salt and other water soluble salts including various sodium, potassium, ammonium, manganese, aluminum, zirconium and magnesium salts such as sulfates, phosphates, acetates, bicarbonates, formates and benzoates.

Liquid vitamin E and/or liquid vitamin E acetate may be provided to supplement the activity of the conditioning and detangling agent that is selected. Vitamin E also softens the skin and promotes growth of the hair coat such as where an animal has a cut or other wound that is healing. Further, a fragrance agent such as vanilla flavoring may be utilized to enhance the appeal of the composition. Vanilla flavoring also advantageously provides a synergistic effect by enhancing the cleaning activity of the composition. In fact, the cleaning activity is so effective that it is not necessary to bathe the animal prior to grooming. Accordingly, this inconvenient and time consuming step may be avoided. As such, cleaning and grooming in cold weather is also possible.

Of course, other known fragrance agents could be included in the composition. Such known agents include, for example, lemon oil, spearmint oil and wintergreen oil.

The following examples are to further illustrate the invention but it is not to be considered as limited thereto.

EXAMPLE 1

840 cc of tap water was placed in a 1 liter mixing vessel. Next 100 cc of isoparaffinic hydrocarbon solvent (available from Chemcentral, Inc. under the trademark ISOPAR C), 25 cc of silicone aqueous emulsion (obtained from Union Carbide Chemical and Plastic Company under the trademark LE-45), 5 cc of liquid vitamin E (vitamin E oil obtained from P. Leiner Nutritional Products, Inc. under the trademark NATURAL LIFE) and 30 cc of vanilla flavoring (obtained from McCormick & Co., Inc. under the trademark McCORMICK) were all added to the water in the vessel. The vessel was then stirred at room temperature to provide the inventive composition.

EXAMPLE 2

790 cc of tap water was placed in a 1 liter mixing vessel. Next 120 cc of isoparaffinic hydrocarbon solvent, 35 cc of silicone aqueous emulsion, 5 cc of liquid E and 50 cc of vanilla flavoring were all added to the water in the vessel. The vessel was then stirred at room temperature to provide the inventive composition.

EXAMPLE 3

900 cc of tap water was placed in a 1 liter mixing vessel. Next 55 cc of isoparaffinic hydrocarbon solvent, 35 cc of silicone aqueous emulsion and 10 cc of vanilla flavoring were all added to the water in the vessel. The vessel was then stirred at room temperature to provide the inventive composition.

EXAMPLE 4

A composition is prepared by substituting quaternary ammonium salt for the silicone aqueous emulsion in Example 1.

EXAMPLE 5

A composition is prepared by substituting sorbitan ester for the silicone aqueous emulsion in Example 1.

EXAMPLE 6

A composition is prepared by substituting potassium acetate for the silicone aqueous emulsion in Example 1.

EXAMPLE 7

A composition is prepared by substituting sodium phosphate for the silicone aqueous emulsion in Example 1.

EXAMPLE 8

A composition is prepared by substituting magnesium bicarbonate for the silicone aqueous emulsion in Example 1.

EXAMPLE 9

A composition is prepared by substituting aluminum formate for the silicone aqueous emulsion in Example 1.

EXAMPLE 10

A composition is prepared by substituting ammonium benzoate for the silicone aqueous emulsion in Example 1.

EXAMPLE 11

A composition is prepared by substituting zirconium sulfate for the silicone aqueous emulsion in Example 1.

I claim:

1. The method of grooming the hair of a domestic animal comprising applying a grooming composition to said hair and subsequently grooming said hair wherein said grooming composition consists essentially of;

79.0%–91.0% water;

5.0% to 12.0% isoparafffinic hydrocarbon solvent degreasing agent miscible in water, said isoparafffinic hydrocarbon solvent having a chain length of between 6 and 14 carbon atoms;

0.5% to 3.5% conditioning and detangling agent miscible in water, selected from the group consisting of linear non-volatile, oil and water silicone aqueous emulsion having a viscosity between 350 and 350,000 Cs, and cyclic non-volatile oil and water silicone aqueous emulsion having a viscosity between 350 and 350,000 Cs;

0.0% to 0.6% vitamin E; and 0.0% and 5.0% fragrance agent.

2. The method claimed in claim 1 wherein said grooming composition includes from about 0.1% to about 0.6% vitamin E.

3. The method claimed in claim 2 wherein said grooming composition comprises at least about 0.01% fragrance agent.

4. The method claimed in claim 1 wherein said isoparafffinic hydrocarbon solvent has a carbon chain of from 7–8 carbon atoms.

* * * * *